United States Patent [19]

Yagihara et al.

[11] 3,950,534
[45] Apr. 13, 1976

[54] FUNGICIDAL COMPOSITION CONTAINING 2-(N-N-BUTYLCARBAMOYLTHIO) ETHYL N¹-N-BUTYL-THIOCARBAMATE

[75] Inventors: Tomio Yagihara; Koshin Miyazaki; Sho Hashimoto, all of Odawara; Akira Wakai, Tokyo, all of Japan

[73] Assignee: Nippon Soda Company, Ltd., Tokyo, Japan

[22] Filed: July 24, 1974

[21] Appl. No.: 491,331

[30] Foreign Application Priority Data
Aug. 1, 1973 Japan............................. 48-85876
Mar. 7, 1974 Japan............................. 49-25713

[52] U.S. Cl.......... 424/300; 260/455 A; 260/468 E; 260/471 C; 260/482 C
[51] Int. Cl.²............................................. A01N 9/12
[58] Field of Search.................................. 424/300

[56] References Cited
UNITED STATES PATENTS

| | | | |
|---|---|---|---|
| 2,384,577 | 9/1945 | Thomas | 260/455 A |
| 2,901,501 | 8/1959 | Wasson et al. | 424/300 |
| 2,937,119 | 5/1960 | Berger et al. | 424/300 |
| 3,385,691 | 5/1968 | Strycker | 424/300 |

*Primary Examiner*—Stanley J. Friedman
*Assistant Examiner*—Allen J. Robinson
*Attorney, Agent, or Firm*—George B. Oujevolk

[57] ABSTRACT

Carbamic acid derivatives of the general formula:

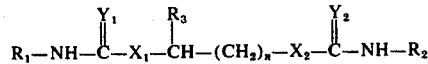

wherein
$R_1$ and $R_2$ are selected from the group consisting of lower alkyl, cycloalkyl, phenyl and phenyl substituted with halogen,
$R_3$ is selected from the group consisting of hydrogen and lower alkyl,
each of $X_1$, $X_2$, $Y_1$ and $Y_2$ is selected from the group consisting of oxygen and sulfur,
n is an integer from 1 to 2, are useful as fungicides.
An exemplary specie is 2-(N-n-butylcarbomoylthio)ethyl N'-n-butylthiolcarbamate.

2 Claims, No Drawings

FUNGICIDAL COMPOSITION CONTAINING 2-(N-N-BUTYLCARBAMOYLTHIO) ETHYL $N^1$-N-BUTYL-THIOCARBAMATE

DETAILED DESCRIPTION OF THE INVENTION

This invention relates to new compound of carbamic acid derivatives, to a process for the preparation thereof and their uses as fungicide.

In particularly this invention relates to new fungicidally active compositions and to method for controlling fungi.

We have discovered that application of the compounds of this invention by the methods of this invention entirely precludes or reduces damage to plants due to fungi. Fungus mycelia are killed or prevented from developing further by the presence of one or more of the compounds, i.e., the compounds are fungicidal.

It has been found that the above outstanding fungicidal activity can be obtained by applying to the locus of fungus infestation, the compounds represented by the following formula:

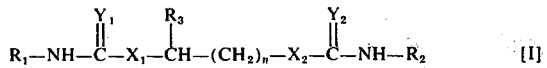

wherein $R_1$ and $R_2$ are selected from the group consisting of lower alkyl, cycloalkyl, phenyl and phenyl substituted with halogen, $R_3$ is selected from the group consisting of hydrogen and lower alkyl, each of $X_1$, $X_2$, $Y_1$ and $Y_2$ is selected from the group consisting of oxygen and sulfur, n is an integer from 1 to 2.

Preferred within the above formula because of its high order of fungicidal activity is:

2-(N-n-butylcarbamoylthio)ethyl N'-n-butylthiolcarbamate.

The compounds of this invention can be prepared by the following equation:

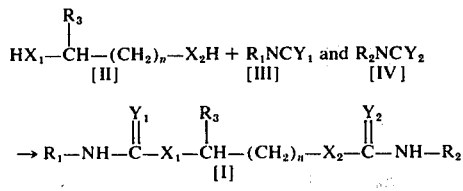

wherein $R_1$, $R_2$, $R_3$, $X_1$, $X_2$, $Y_1$, $Y_2$ and n represent the aforesaid meanings.

The above reaction can be conducted in the presence of tertiary amine such as triethylamine and trimethylamine or alkali carbonate and sodiumbicarbonate in an inert solvent.

As an inert solvent, acetone, ether, benzene, chlorinated hydrocarbon etc.

Reaction temperature is from 10°C to the boiling point of employed solvent and the reaction terminates between two and several hours.

After the end of the reaction, the precipitate is isolated from the reaction mixture by the evaporation of the solvent.

The isolated compound may be purified by recrystallizing from an organic solvent.

The product is identified by means of an elementary analysis, NMR spectrum and IR spectrum.

The following examples are presented by way of illustration of the preparation of the compounds of the present invention and are not intended to limit the scope of this invention:

EXAMPLE 1

Preparation of 2-(N-n-butylcarbamoylthio)ethyl N'-n-butylcarbamate 2-mercaptoethanol (7.8 g) and triethylamine (1.0 g) were dissolved in acetone (30 ml) and the mixture was stirred while adding slowly n-butylisocyanate (20 g) dissolved in acetone (30 ml).

After refluxing 3 hours, the acetone was removed at reduced pressure and 2-(N-n-butylcarbamoylthio)ethyl N'-n-butylcarbamate having a melting point of 98° to 99°C was obtained as while crystal by recrystallizing the residue from the mixture of acetone and n-hexane.

Yield amount: 25.5 g (93.3 % of yield rate)

Elemental analysis — Calculated for $C_{12}H_{24}N_2O_3S$ (%) : C 52.17, H 8.69, N 10.14, S 11.59; Found (%) : C 52.06, H 8.69, N 9.92, S 11.31.

Infrared spectrum — NH (3295 $cm^{-1}$), CO (1635 $cm^{-1}$).

EXAMPLE 2

Preparation of 2-(N-n-butylcarbamoylthio)ethyl N'-n-butylthiolcarbamate

The same reaction procedures as Example 1 were carried out by using 1,2-ethandithiol (9.4 g) and n-butylisocyanate (20 g), and thereby 2-(N-n-butylcarbamoylthio)ethyl N'-n-butylthiolcarbamate having a melting point of 152° to 153°C was obtained as colorless needles.

Yield amount: 27 g (92.3 % of yield rate)

Elemental analysis — Calculated for $C_{12}H_{24}N_2O_2S_2$(%) : C 49.32, H 8.22, N 9.55, S 21.92; Found (%): C 49.32, H 8.40, N 9.77, S 22.19.

Infrared spectrum — NH(3300 $cm^{-1}$), CO(1632 $cm^{-1}$).

EXAMPLE 3

Preparation of 3-(N-n-butylthiocarbamoylthio)propyl N'-n-butyldithiocarbamate 1,3-propandithiol (1.0 g) and a little amount of triethylamine were dissolved in acetone (10 ml) and the mixture was stirred while adding slowly n-butylthioisocyanate (2.5 g) at room temperature. After the reaction solution ws permitted to stand for a day at room temperature, acetone was removed at reduced pressure and the precipitate was the crude product.

3-(N-n-butylthiocarbamoylthio)propyl N-n-butyldithiocarbamate having a melting point of 70.5° to 71.5° was obtained by recrystallizing the crude product by the mixture of aceton and n-cyclohexane.

Yield amount: 3.1 g (92 % of yield rate)

EXAMPLE 4

Preparation of 2-methyl-2(N-n-butylcarbamoylthio)ethylthio N'-n-butylcarbamate

The same reaction proceudres as Example 3 were carried out by using 2-butylisocyanate (2.2 g), and thereby 2-methyl-2(N-n-butylcarbamoylthio)ethylthio N'-n-butylcarbamate having a melting point of 120° to 121.5°C ws obtained.

Yield amount: 2.9 g (94.7 % of yield rate)

Examples of the compounds which can be used in the present invention are listed in the Table 1.

The compounds of the invention control a wide variety of fungus diseases of foliage, fruit, stems and roots of growing plants without damage to the host.

The many fungi against which the compounds of this invention are active may be represented by, but is not intended to be limited to, the following:

Table 1

| Compound No. | Chemical Formula | Melting Point (°C) |
|---|---|---|
| 1 | $CH_3-NH-\overset{S}{\underset{\parallel}{C}}-S-CH_2CH_2-S-\overset{S}{\underset{\parallel}{C}}-NH-CH_3$ | 138 – 139 |
| 2 | $CH_3-NH-\overset{O}{\underset{\parallel}{C}}-S-CH_2CH_2-O-\overset{O}{\underset{\parallel}{C}}-NH-CH_3$ | 86 – 87.5 |
| 3 | $CH_3-NH-\overset{O}{\underset{\parallel}{C}}-S-CH_2CH_2-O-\overset{O}{\underset{\parallel}{C}}-NH-(CH_2)_3CH_3$ | 54 – 56 |
| 4 | $CH_3-NH-\overset{O}{\underset{\parallel}{C}}-O-CH_2CH_2-S-\overset{O}{\underset{\parallel}{C}}-NH-(CH_2)_3CH_3$ | 91.5 – 92.5 |
| 5 | $CH_3CH_2-NH-\overset{O}{\underset{\parallel}{C}}-S-CH_2CH_2-O-\overset{O}{\underset{\parallel}{C}}-NH-CH_2CH_3$ | 100 – 101 |
| 6 | $CH_3(CH_2)_2-NH-\overset{O}{\underset{\parallel}{C}}-S-CH_2CH_2-O-\overset{O}{\underset{\parallel}{C}}-NH-(CH_2)_2CH_3$ | 106 – 108 |
| 7 | $CH_3(CH_2)_2-NH-\overset{O}{\underset{\parallel}{C}}-O-CH_2CH_2-S-\overset{O}{\underset{\parallel}{C}}-NH-(CH_2)_3CH_3$ | 73 – 75 |
| 8 | $CH_3(CH_2)_3-NH-\overset{O}{\underset{\parallel}{C}}-O-CH_2CH_2-O-\overset{O}{\underset{\parallel}{C}}-NH-(CH_2)_3CH_3$ | 93 – 95 |
| 9 | $CH_3(CH_2)_3-NH-\overset{O}{\underset{\parallel}{C}}-S-CH_2CH_2-O-\overset{O}{\underset{\parallel}{C}}-NH-(CH_2)_3CH_3$ | 98 – 99 |
| 10 | $CH_3(CH_2)_3-NH-\overset{O}{\underset{\parallel}{C}}-S-CH_2CH_2-S-\overset{O}{\underset{\parallel}{C}}-NH-(CH_2)_3CH_3$ | 152 – 153 |
| 11 | $CH_3(CH_2)_3-NH-\overset{S}{\underset{\parallel}{C}}-S-CH_2CH_2-S-\overset{S}{\underset{\parallel}{C}}-NH-(CH_2)_3CH_3$ | 103 – 104 |
| 12 | $C_6H_5-NH-\overset{O}{\underset{\parallel}{C}}-S-CH_2CH_2-O-\overset{O}{\underset{\parallel}{C}}-NH-C_6H_5$ | 171 – 172 |
| 13 | $CH_3-NH-\overset{O}{\underset{\parallel}{C}}-S-CH_2CH_2-O-\overset{O}{\underset{\parallel}{C}}-NH-C_6H_5$ | 100 – 104 |
| 14 | $CH_3-NH-\overset{O}{\underset{\parallel}{C}}-S-CH_2CH_2-O-\overset{O}{\underset{\parallel}{C}}-NH-C_6H_4-Cl$ | 158 – 159.5 |
| 15 | $(o\text{-}Cl\text{-}C_6H_4)-NH-\overset{O}{\underset{\parallel}{C}}-S-CH_2CH_2-O-\overset{O}{\underset{\parallel}{C}}-NH-(o\text{-}Cl\text{-}C_6H_4)$ | 105 – 108 |
| 16 | $(Cl\text{-}C_6H_4)-NH-\overset{O}{\underset{\parallel}{C}}-S-CH_2CH_2-O-\overset{O}{\underset{\parallel}{C}}-NH-(C_6H_4\text{-}Cl)$ | 179 – 181 |
| 17 | $CH_3(CH_2)_3-NH-\overset{O}{\underset{\parallel}{C}}-S-(CH_2)_3-S-\overset{O}{\underset{\parallel}{C}}-NH-(CH_2)_3CH_3$ | 92 – 93 |
| 18 | $CH_3(CH_2)_3-NH-\overset{S}{\underset{\parallel}{C}}-S-(CH_2)_3-S-\overset{S}{\underset{\parallel}{C}}-NH-(CH_2)_3CH_3$ | 70.5 – 71.5 |
| 19 | $CH_3(CH_2)_3-NH-\overset{O}{\underset{\parallel}{C}}-S-\underset{\underset{CH_3}{\vert}}{CH}-CH_2-S-\overset{O}{\underset{\parallel}{C}}-NH-(CH_2)_3CH_3$ | 120 – 121.5 (d.) |
| 20 | $CH_3(CH_2)_3-NH-\overset{S}{\underset{\parallel}{C}}-S-\underset{\underset{CH_3}{\vert}}{CH}-CH_2-S-\overset{S}{\underset{\parallel}{C}}-NH-(CH_2)_3CH_3$ | 98 – 99 |
| 21 | $CH_3(CH_2)_3-NH-\overset{O}{\underset{\parallel}{C}}-O-\underset{\underset{CH_3}{\vert}}{CH}-CH_2-S-\overset{O}{\underset{\parallel}{C}}-NH-(CH_2)_3CH_3$ | 83 – 84 | d.: decomposition

As mentioned previously, it has been found that the compounds of the invention posses outstanding fungicidal activity when employed to prevent damage to plants. The paragraphs which follow describe in more detail the utility of this invention.

Damping-off (*Phizoctonia spp.,*) and
Late blight (*Phytophthora infestans*) of vegetables, and
Alternaria blotch (*Alternaria mali*) of fruits ets., and particularly effective against Damping-off of vegetables.

It is another advantage that the compounds of the present invention have low toxicity for warm-blooded animals and fish.

The method of the present invention comprehends the employment of a liquid or solid composition containing one or more of the present compounds as an active component.

The compound can be used directly without mixing with suitable carriers.

The active ingredient of this invention may be formulated by mixing with suitable carriers in a form generally used in pesticidal compositions such as wettable powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, xylene, cyclohexane, cyclohexanone, dimethyl-formamide, dimethylsulfoxide, alcohol, acetone, benzene and others are used. Sometimes surface active agent is added in order to give a homogeneous and stable formulation.

The concentrations of the active ingredients in the fungicidal composition of this invention vary according to type of formulation and they are, for example, used in a range of 5 – 80 weight percent, preferably 20 – 80 weight percent, in wettable powders, 5 – 70 weight percent, preferably 10 – 50 weight percent, in emulsifiable concentrates, and 0.5 – 20 weight percent, preferably 1 – 10 weight percent in dust formulations.

Incidentally, wettable powder or emulsifiable concentrate containing proper quantity of the active compound is suspended or emulsified in water and then sprayed to the foliages of the weeds or to the soil around the cultivated plants. Furthermore, the compounds may be used as a mixture with other fungicides, insecticides, acaricides and herbicide.

Some examples in this invention are stated below. But the main compounds and the additives are not defined limitedly by these Examples.

EXAMPLE 5

Wettably Powder

|  | Parts by weight |
|---|---|
| Compound No. 1 | 40 |
| Sodium alkylsulfonate | 7 |
| Diatomaceous earth | 53 |

These are mixed homogeneously and reduced to fine particles. Consequently, wettable powder containing 40% of the active ingredient is obtained. In practical use, it is diluted to a certain concentration with water and is sprayed as a suspension.

EXAMPLE 6

Emulsifiable Concentrate

|  | Part by weight |
|---|---|
| Compound No. 2 | 30 |
| Polyoxyethylenealkylarylether | 8 |
| Xylene | 42 |
| Dimethylformamide | 20 |

These are mixed and dissolved. Consequently, emulsifiable concentration containing 30% of the active ingredient is obtained. In practical use, it is diluted to certain concentration with water and then is sprayed as an emulsion.

EXAMPLE 7

Dust Formulation

|  | Part by weight |
|---|---|
| Compound No. 3 | 10 |
| Talc | 90 |

These are mixed homogeneously, reduced to fine particles. Consequently, dust formulation containing 10% of the active ingredient is obtained. In practical use, it is directly applied.

The superior fungicidal activity of compounds of this invention is clearly illustrated by the following tests.

Test 1

Cucumber was grown in pots.

10 g culture medium consisting of the mash and chaff in which *Rhizoctonia spp.*, has been cultured was mixed with 300 g of normal soil. 20 g of said mixture was put in a pot when cotyledon of cucumber was developed and 10 ml of water-diluted solution of the wettable powder containing the test compound was poured in the pot at a rate of 2.6 liters per one squre meters.

5 days later, a number of disease was counted and evaluation of percent disease control was based on the percentage of diesase on the untreated check. Each test was repeated three times for each concentration. The result was shown in Table 2.

Table 2

| Test compound | 500ppm | 300ppm | Control Value (%) 250ppm | 150ppm | 125ppm | 75ppm |
|---|---|---|---|---|---|---|
| 9 | — | 100 | — | 83 | — | 60 |
| 10 | — | 100 | — | 85 | — | 81 |
| 11 | — | 100 | — | 85 | — | 60 |
| 17 | 86 | — | 64 | — | 64 | — |
| 18 | 100 | — | 57 | — | 86 | — |
| 19 | 100 | — | 100 | — | 93 | — |
| 20 | 100 | — | 100 | — | 100 | — |
| PCNB* | — | 95 | — | 78 | — | 20 |
| Untreated |  |  | 0 |  |  |  |

*pentachloronitrobenzene

Test 2

Tomato was grown in pots and its leaf was cut off. Cut leaf was immersed for 30 to 60 seconds into water diluted solution of the wettable powder containing test compound in the concentration of 500 ppm.

After drying, the leaf was inoculated with the zoo spore suspension of late blight (*Phytophthora infestans*)

in the concentration 100,000/ml and placed for 2 days at 28°C.

Two days after inoculation, the disease degree was examined and evalvation of percent disease control was based on the percentage of disease on the untreated check.

Each test was repeated three times for each concentration. The result was shown in Table 3.

Table 3

| Test compound | Concentrationn of active ingredient (ppm) | Control Value (%) |
| --- | --- | --- |
| 7 | 500 | 99 |
| 9 | 500 | 98 |
| 13 | 500 | 100 |
| 18 | 500 | 87 |
| Comparative compound* | 500 | 86 |

Table 3-continued

| Test compound | Concentrationn of active ingredient (ppm) | Control Value (%) |
| --- | --- | --- |
| Untreated | — | 0 |

*N-(1,1,2,2-tetrachloroethylthio)-4-cyclohexene-1,2-dicarboxyimido

What is claimed is:

1. A fungicidal composition for combatting plant fungi comprising an inert carrier and a fungicidally effective amount of the compound of the formula

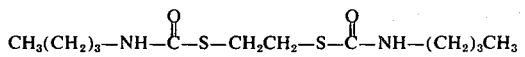

2. A method of controlling plant fungi comprising applying to the locus to be protected a fungicidally effective amount of the compound of the formula

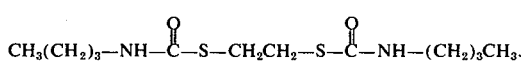

* * * * *